(12) United States Patent
Vautravers et al.

(10) Patent No.: US 10,487,194 B2
(45) Date of Patent: Nov. 26, 2019

(54) MIXTURE OF N-(1,3-BENZOTHIAZOL-2-YLSULFANYL)-2-METHYL-CYCLOHEXANAMINE AND N-(1,3-BENZOTHIAZOL-2-YLSULFANYL)-4-METHYL-CYCLOHEXANAMINE

(71) Applicant: BASF SE, Ludwigshafen (DE)

(72) Inventors: Nicolas Vautravers, Strasbourg (FR); Joaquim Henrique Teles, Waldsee (DE); Fritz Nimtz, Wiesloch (DE); Alexander Panchenko, Ludwigshafen (DE); Frank Hettche, Weinheim (DE); Klaus Breuer, Speyer (DE); Martin Ernst, Heidelberg (DE); Hidehiko Mizuno, Hong Kong (CN); Rajendra Sundar, Morristown, NJ (US)

(73) Assignee: BASF SE, Ludwigshafen (DE)

( * ) Notice: Subject to any disclaimer, the term of this patent is extended or adjusted under 35 U.S.C. 154(b) by 131 days.

(21) Appl. No.: 15/746,183

(22) PCT Filed: Jul. 13, 2016

(86) PCT No.: PCT/EP2016/066602
§ 371 (c)(1),
(2) Date: Jan. 19, 2018

(87) PCT Pub. No.: WO2017/012937
PCT Pub. Date: Jan. 26, 2017

(65) Prior Publication Data
US 2018/0208745 A1    Jul. 26, 2018

Related U.S. Application Data

(60) Provisional application No. 62/195,306, filed on Jul. 22, 2015.

(51) Int. Cl.
*C08K 5/47* (2006.01)
*C08K 5/44* (2006.01)
(Continued)

(52) U.S. Cl.
CPC ............. *C08K 5/47* (2013.01); *C07D 277/80* (2013.01); *C08K 5/0025* (2013.01); *C08K 5/44* (2013.01);
(Continued)

(58) Field of Classification Search
CPC .. C07D 277/00; C07D 277/60; C07D 277/62; C07D 277/68; C07D 277/70; C07D 277/76; C07D 277/80; C08K 5/0025; C08K 5/44; C08K 5/47; C08K 2201/014; C07C 381/00; C08L 7/00; C08L 9/00; C08L 11/00; C08L 13/00; C08L 15/00; C08L 17/00; C08L 19/00; C08L 21/00
See application file for complete search history.

(56) References Cited

U.S. PATENT DOCUMENTS 2,382,793 A * 8/1945 Howland ............. C07D 277/80
548/167
2,822,367 A * 2/1958 Alliger ................. C07D 277/80
548/167
(Continued)

FOREIGN PATENT DOCUMENTS

| CS | 176039 B1 | 1/1979 |
| EP | 0443344 A2 | 8/1991 |
| EP | 1449837 A1 | 8/2004 |
| EP | 2256157 A1 | 12/2010 |
| FR | 2.037.001 | 12/1970 |
| WO | 2008/035375 A2 | 3/2008 |

OTHER PUBLICATIONS

International Search Report dated Oct. 6, 2016, in PCT/EP2016/066602, filed Jul. 13, 2016.

*Primary Examiner* — Kregg T Brooks
(74) *Attorney, Agent, or Firm* — Oblon, McClelland, Maier & Neustadt, L.L.P.

(57) ABSTRACT

A composition comprising compound (I) of formula and compound (II) of formula wherein $R^{2a}$ and $R^{2b}$ independently from each other are a linear alkyl group with 1 to 4 carbon atoms and $R^{1a}$, $R^{1b}$, $R^{3a}$ to $R^{6a}$ and $R^{3b}$ to $R^{6b}$ independently from each other are a hydrogen atom or a linear alkyl group with 1 to 4 carbon atoms.

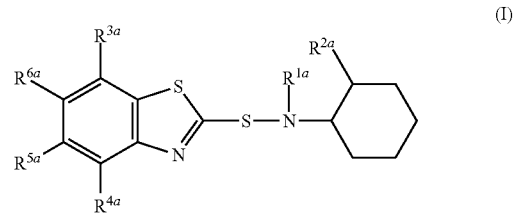

(I)

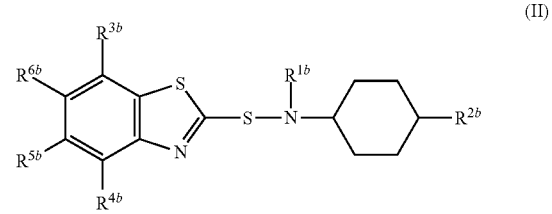

(II)

7 Claims, No Drawings

(51) Int. Cl.
*C08L 7/00* (2006.01)
*C08L 21/00* (2006.01)
*C07D 277/80* (2006.01)
*C08K 5/00* (2006.01)

(52) U.S. Cl.
CPC ............. *C08L 7/00* (2013.01); *C08L 21/00* (2013.01); *C08K 2201/014* (2013.01)

(56) References Cited

U.S. PATENT DOCUMENTS

2004/0167340 A1 8/2004 Grabowski et al.
2010/0234535 A1 9/2010 Inamdar et al.
2011/0021674 A1 1/2011 Satou \* cited by examiner

MIXTURE OF N-(1,3-BENZOTHIAZOL-2-YLSULFANYL)-2-METHYL-CYCLOHEXANAMINE AND N-(1,3-BENZOTHIAZOL-2-YLSULFANYL)-4-METHYL-CYCLOHEXANAMINE

The present invention relates to a composition comprising compound (I) of formula

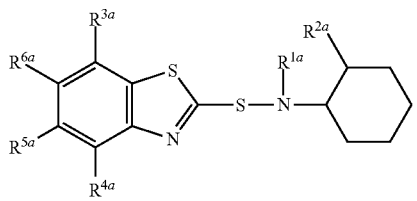

and
compound (II) of formula

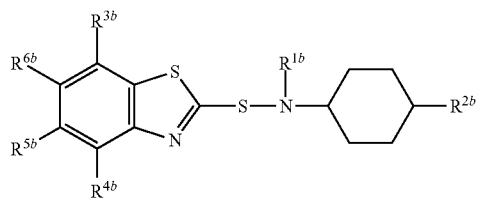

wherein $R^{2a}$ and $R^{2b}$ independently from each other are a linear alkyl group with 1 to 4 carbon atoms and $R^{1a}$, $R^{1b}$, $R^{3a}$ to $R^{6a}$ and $R^{3b}$ to $R^{6b}$ independently from each other are a hydrogen atom or a linear alkyl group with 1 to 4 carbon atoms Benzothiazolylsulfenamides may be used as vulcanization accelerators. A standard vulcanization accelerator is, for example benzothiazolylsulfenamide is N-(1,3-benzothiazol-2-ylsulfanyl)cyclohexanamine, shortly referred to as CBS. A process for the synthesis of CBS by reacting primary amines with salts of mercapto benzothiazol is described in EP-A 1449 837. CBS is a solid with a melting point of from 96 to 102° C. (1 bar).

EP-A 2256 157 discloses derivatives of N-(1,3-benzothiazol-2-ylsulfanyl)-cyclohexanamine and their use as vulcanization accelerator.

N-(1,3-benzothiazol-2-ylsulfanyl)-2-methyl-cyclohexanamine and its use as vulcanization accelerator is known from CS 176039.

EP-A 443 344 describes the hydrogenation of mixtures of 2,4- and 2,6 toluene diamine to a mixture of 2,4-methyl cyclohexandiamine and 2,6-methyl cyclohexandiamine.

It is the object of the invention to find alternative vulcanization which may be prepared easily and at low costs and which are highly effective as accelerators in rubber compositions.

Accordingly, the composition defined above and the use of such composition as vulcanization accelerator have been found.

To the Composition

The composition comprises compound (I) of formula

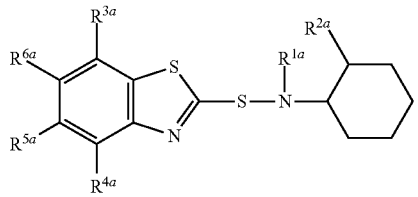

and
compound (II) of formula

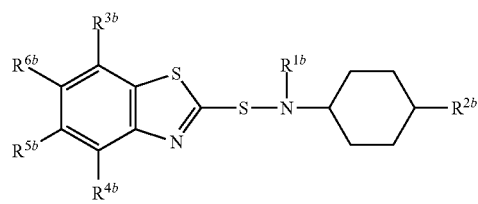

wherein $R^{2a}$ and $R^{2b}$ independently from each other are a linear alkyl group with 1 to 4 carbon atoms and $R^{1a}$, $R^{1b}$, $R^{3a}$ to $R^{6a}$ and $R^{3b}$ to $R^{6b}$ independently from each other are a hydrogen atom or a linear alkyl group with 1 to 4 carbon atoms Preferably both $R^{2a}$ and $R^{2b}$ are identical and are in particular a methyl group.

$R^{1a}$, $R^{1b}$, $R^{3a}$ to $R^{6a}$ and $R^{3b}$ to $R^{6b}$ may in particular independently from each other be a hydrogen atom or a methyl or ethyl group.

Preferably, $R^{1a}$ is identical to $R^{1b}$ and $R^{3a}$ to $R^{6a}$ are identical to and $R^{3b}$ to $R^{6b}$.

Most preferably all of $R^{1a}$, $R^{1b}$, $R^{3a}$ to $R^{6a}$ and $R^{3b}$ to $R^{6b}$ are a hydrogen atom.

Compound (I) may be a mixture of different compounds (I) as well as compound (II) may be a mixture of different compounds (II).

Most preferably compound (I) is N-(1,3-benzothiazol-2-ylsulfanyl)-2-methyl-cyclohexanamine, shortly referred to as compound (Ia), which has the formula

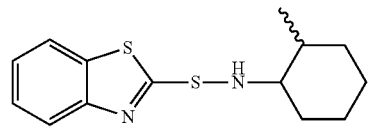 [SMILES: CC1CCCCC1NSc1nc2ccccc2s1]

Most preferably compound (II) is N-(1,3-benzothiazol-2-ylsulfanyl)-4-methyl-cyclohexanamine, shortly referred to as compound (IIa), which has the formula

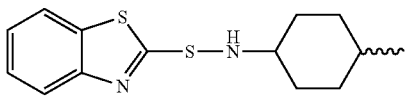 [SMILES: CC1CCC(NSc2nc3ccccc3s2)CC1]

The methyl group which is the substituent to the cyclohexyl group may have a cis or trans stereoisomerism. Preferably each of compound Ia and IIa are a mixture of compounds with a cis and trans substituted methyl group (indicated by the wiggly line in the above formulas).

Preferably, the composition comprises compound (I) and (II) in a weight ratio of from 1:10 to 10:1, in particular in a weight ratio of from 1:3 to 3:1.

In a particularly preferred embodiment of the invention, the composition comprises compound (I) and (II) in a weight ratio of from 1:2 to 2:1.

In a particularly preferred embodiment of the invention the composition comprises more of compound I than of compound II.

Most preferred is the composition comprising compound (I) and (II) in a weight ratio of 2:1 to 1:1, in particular about 1.5:1 corresponding to 60 weight % of (I) and 40 weight % of (II), based on the sum of (I) and (II).

The composition may comprise other components, for examples such as solvents, or additives like stabilizers.

Preferably, the composition consists to at least 50% by weight, in particular to at least 70% by weight and more preferably at least 90% by weight, respectively 98% by weight of compounds (I) and (II).

Preferably, the composition is liquid at 20° C., normal pressure (1 bar).

In a most preferred embodiment the composition consists of compounds (I) and (II), only, such composition with 60 weight % of (I) and 40 weight % of (II), based on the sum of (I) and (II) is fluid at 20° C., 1 bar.

To the Synthesis of Compounds (I) and (II)

The preparation compounds (I) and (II) may be done according to the preparation of benzothiazolylsulfenamides as described, for example in US 2004/0167340.

Accordingly, mercaptobenzothiazoles or the alkali metal salts or dimers thereof are preferably reacted with primary or secondary amines and thereafter with an oxidizing agent such as chlorine, hypochlorite, H2O2 or a combination of oxidizing agents.

The mercaptobenzothiazoles used for the preparation of compounds (I) and (II) is a mercaoptobenzothiazole with substituents $R^{3a}$ to $R^{6a}$ respectively $R^{3b}$ to $R^{6b}$ as defined above. Preferably, mercaptobenzothiazole (all of $R^{3a}$ to $R^{6a}$ respectively $R^{3b}$ to $R^{6b}$ are hydrogen) as such is used.

The amine used is a methyl substituted cyclohexylamine, which may be a primary amine ($R^{1a}$ respectively $R^{1b}$ are hydrogen) or a secondary amine ($R^{1a}$ respectively $R^{1b}$ are a linear alkyl group with 1 to 4 carbon atoms).

Preferably the methyl substituted cyclohexylamine used is a primary amine ($R^{1a}$ respectively $R^{1b}$ are hydrogen).

Compounds (I) and (II) differ in the position of $R^{2a}$ and $R^{2b}$ in the cyclohexyl ringsystem.

Compounds (I) and (II) may be produced separately using a different cyclohexylamine, a cyclohexylamine with $R^{2a}$ for compound (I) and a cyclohexylamine with $R^{2b}$ for compound (II).

The separately obtained compounds (I) and (II) may be mixed thereafter to obtain the composition.

In a preferred embodiment of the invention a mixture of a cycloheylamine with $R^{2a}$ and a cyclohexylamine with $R^{2b}$ is used in the preparation process. The composition of such mixture should correspond to the desired amounts of compound (I) and (II) in the composition.

Hence the composition is easily obtained.

The mixture of cyclohexylamines corresponding to the preferred and most preferred ratio of compounds (I) and (II) as defined above is available from a mixture of 2,4- and 2,6 diamine-toluol by the known hydrogenation of the ring system to 2,4- and 2,6 Methyl-cyclohexyl-diamine according to

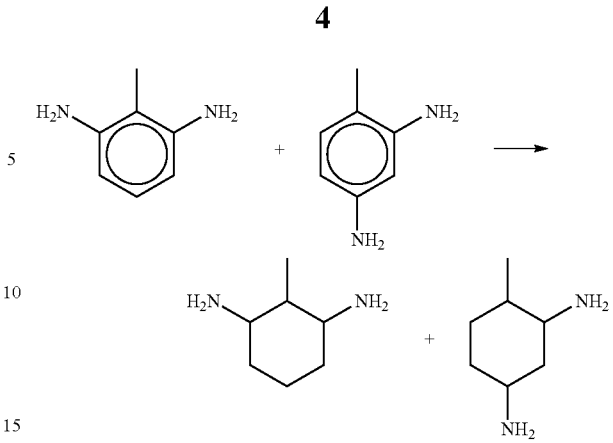

In this process a side reaction occurs wherein the forestanding diamines lose one amino group giving a mixture of ortho- and para-methyl cyclohexylamin in a mixture of about 60% by weight ortho-cyclohexylamine and 40% by weight para-cyclohexylamine.

The obtained mixture of ortho-cyclohexylamine and para-cyclohexylamine may be used in the reaction with the mercaptobenzothiazole.

The mercaptobenzothiazoles and cyclohexylamines may be used in equivalent amounts or excess. Preferably the mercaptobenzothiazoles and cyclohexylamines are used in amounts corresponding to from 1:3 to 3:1, more preferably 1:2 to 2:1 equivalents of mercaptobenzothiazoles to cycylohexyamines.

The reaction is preferably performed in a hydrophilic solvent which is most preferably water.

In order to adjust the pH an acid may be added, for example sulfuric acid.

The reaction between the mercaptobenzothiazoles and cyclohexylamines may, for example, be performed at temperatures from 10 and 100° C., in particular from 20 to 60° C., in particular between 30 and 50° C.

The oxidizing agent may be added thereafter. The preferred oxidizing agent is sodium hypochlorite, $H_2O_2$ or combinations thereof. The oxidation may be performed at suitable temperatures of 5 to 50° C., preferably the oxidation is performed at room temperature. Cooling of the reaction mixture might be required.

Finally two phases are obtained, one organic phase which is the desired product and an aqueous phase. The phases are separated and the organic phase may be purified by usual methods as filtration of solids and optionally distillation.

To the Use of the Composition as Accelerator in Rubber

The composition comprising compound (I) and (II) may be used as accelerator in rubber.

The rubber may be any rubber, as well as a natural or a synthetic rubber. Preferably, the rubber is a compound with at least one double bond which can be crosslinked by an accelerator which is a sulfur compound, in particular elementary sulfur.

Natural rubber is a polymer of isoprene.

Synthetic rubber may be, for example, a synthetic polyisoprene, a polybutadiene, a styrene-butadiene copolymer, an acrylnitril-butadiene copolymer, an ethylene-propylene-diene copolymer or a polychloroprene.

The rubber composition comprises the composition comprising compound (I) and (II) as accelerator.

The rubber composition should preferably comprise a vulcanization agent, which is in particular sulfur, and the composition comprising compound (I) and (II) as accelerator.

Preferably, the rubber composition comprises from 0.05 to 5% by weight of the composition, in particular the rubber composition comprises from 0.1 to 3% by weight, more preferably from 0.2 to 2% by weight, most preferred from 0.2 to 1% by weight of the composition as accelerator. The rubber composition may be comprise further additives. Further additives are in particular fillers and pigments, for example carbon black.

The rubber composition may be prepared according to standard mixing procedures, for example by kneading the components in as standard equipment like a Banbury mixer.

Vulcanization of the rubber composition may be performed as usual at elevated temperatures.

The rubber composition may be used in any technical applications such as, for example for treads of tires for cars, trucks and busses, bicycles and motorcycles, two wheel vehicles, any hoses, belt conveyors and rubber coatings of metals.

The products made from the rubber composition may in particular comprise other materials, for example reinforcing materials, in particular steel cords which are covered by the vulcanized rubber composition.

The composition comprising compound (I) and (II) is preferably liquid which has advantages in handling and application of the composition. The composition has at least the same level of reactivity in vulcaniziation resulting in the equivalent properties of the vulcanized products as standard accelerators used so far.

EXAMPLES

Products Used in the Examples

N-(1,3-benzothiazol-2-ylsulfanyl)-2-methyl-cyclohexanamine and N-(1,3-benzothiazol-2-ylsulfanyl)-4-methyl-cyclohexanamine in a weight ratio of about 60:40, shortly referred to as Accelerator 1

For comparison: N-(1,3-benzothiazol-2-ylsulfanyl)cyclohexanamine which is solid at 20° C. (1 bar), shortly referred to as CBS Neorub is a natural 1,4 polyisopren rubber.

Sulfur is elementary sulfur having S8 modification.

Example 1—Preparation of Accelarator I

A mixture of ortho-cyclohexylamine and para-cyclohexylamine (25.1 g, about 60% ortho and 40% para) was added to sodium mercaptobenzothiazole (20 wt.-%, 30 g) and the solution (pH=12.3) was heated to 40° C. $H_2SO_4$ (20 wt. %, 34.8 g) was added over 30 minutes to sink the pH till 10.6. $H_2O_2$ (10 wt.-%, 52.3 g) was then added over 30 minutes followed by the addition of NaOCl (14 wt.-%, 28.7 g) over 30 minutes. NaOH conc. (5.8 g) was finally added to higher the pH of the solution to 11.6. The phases were separated and the organic one diluted with $CH_2Cl_2$ and washed with water. The crude residue was filtered through silica gel leaving a yellow oil after solvent removal (17.6 g).

Example 2—Suitability of Accelerator I for Rubber

In order to test the potency Accelerator I in comparison to the known standard accelerator CBS as a vulcanization accelerator a standard rubber compound based on natural rubber was manufactured according to DIN 53 670 part 2 (Testing of rubber and elastomers; testing of rubber in standard test mixes; natural rubber (NR)).

In a first step a base compound without any accelerator has been prepared on a roller mill by mixing procedure according to DIN 53 670 as listed in table 1.

TABLE 1 composition of base compound

|  | phr | gram |
|---|---|---|
| Neorub | 100 | 1500 |
| Carbon Black | 30 | 450 |
| ZnO | 5 | 75 |
| Stearic Acid | 2 | 30 |
| Sulfur | 2.3 | 34.5 |
| Total | 139.3 | 2090 |

The base compound has been divided in three parts:

Test system A without vulcanization accelerator

Test system B with accelerator CBS

Test system C with Accelerator I.

To each test system the accelerators and further additives as listed in table 2 were added. The preparation of the test systems has been carried out according to DIN 53 670 part 2.

TABLE 2

|  | A | | B | | C | |
|---|---|---|---|---|---|---|
|  | phr | gram | phr | gram | phr | gram |
| Base compound | 139.3 | 696.5 | 139.3 | 696.5 | 139.3 | 696.5 |
| Carbon Black | 5 | 25 | 5 | 25 | 5 | 25 |
| CBS |  |  | 0.7 | 3.5 |  |  |
| Accelerator 1 |  |  |  |  | 0.7 | 3.5 |
| Total | 144.3 | 721.5 | 145 | 725 | 145 | 725 |

Vulcanization Tests

All compounds have been tested in a rotorless vulcameter (MDR 2000) according to DIN 53 529 part 3 at temperatures of 140° C. and 160° C.

Vulcanization occurs in the vulcameter. An increase of viscosity and torsional moment is observed with proceeding crosslinking. Results are shown in Figure A and Figure B. A high torsional moment corresponds to a high fraction of crosslinked rubber.

Figure A shows the increase of the torsional moment (Nm) over time (minutes) at 140° C.

Figure B shows the increase of the torsional moment (Nm) over time (minutes) at 160° C.

The invention claimed is:

1. A composition, comprising: compound (I) of formula:

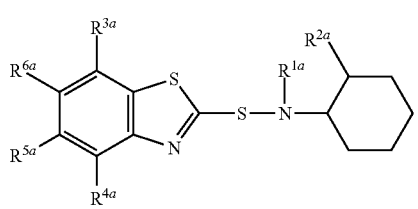

and
a compound (II) of formula:

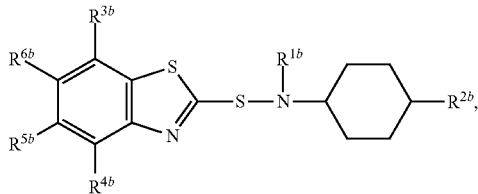

wherein $R^{2a}$ and $R^{2b}$ independently from each other are a linear alkyl group with 1 to 4 carbon atoms and $R^{1a}$, $R^{1b}$, $R^{3a}$ to $R^{6a}$ and $R^{3b}$ to $R^{6b}$ independently from each other are a hydrogen atom or a linear alkyl group with 1 to 4 carbon atoms wherein a weight ratio of the compound (I) to the compound (II) is from 1:10 to 10:1.

2. The composition according claim 1, wherein both $R^{2a}$ and $R^{2b}$ are a methyl group.

3. The composition according to claim 1, wherein $R^{1a}$, $R^{1b}$, $R^{3a}$ to $R^{6a}$ and $R^{3b}$ to $R^{6b}$ are a hydrogen atom.

4. The composition according to any of claim 1, wherein a weight ratio of the compound (I) to the compound (II) is from 1:3 to 3:1.

5. The composition according to claim 1, comprising: at least 50% by weight of the compounds (I) and (II).

6. A method for accelerating vulcanization, the method comprising: accelerating vulcanization with the composition according to claim 1 as a vulcanization accelerator.

7. A rubber composition, comprising:
the composition according to claim 1.

* * * * *